United States Patent
Baeuerle

(10) Patent No.: US 11,229,385 B2
(45) Date of Patent: Jan. 25, 2022

(54) IDENTIFYING AND MEASURING BODILY STATES AND FEEDBACK SYSTEMS BACKGROUND

(71) Applicant: COGNIFISENSE, INC., Sunnyvale, CA (US)

(72) Inventor: Tassilo Baeuerle, Sunnyvale, CA (US)

(73) Assignee: COGNIFISENSE, INC., Sunnyvale, CA (US)

(*) Notice: Subject to any disclaimer, the term of this patent is extended or adjusted under 35 U.S.C. 154(b) by 25 days.

(21) Appl. No.: 16/463,289

(22) PCT Filed: Nov. 22, 2017

(86) PCT No.: PCT/US2017/063029
§ 371 (c)(1),
(2) Date: May 22, 2019

(87) PCT Pub. No.: WO2018/098289
PCT Pub. Date: May 31, 2018

(65) Prior Publication Data
US 2019/0307384 A1 Oct. 10, 2019

Related U.S. Application Data

(60) Provisional application No. 62/425,858, filed on Nov. 23, 2016, provisional application No. 62/425,865, (Continued)

(51) Int. Cl.
*A61B 5/16* (2006.01)
*A61B 5/0533* (2021.01)
(Continued)

(52) U.S. Cl.
CPC .......... *A61B 5/163* (2017.08); *A61B 5/0533* (2013.01); *A61B 5/1103* (2013.01);
(Continued)

(58) Field of Classification Search
CPC ..... A61B 5/163; A61B 5/0533; A61B 5/1103; A61B 5/1114; A61B 5/1123; A61B 5/165;
(Continued)

(56) References Cited

U.S. PATENT DOCUMENTS

| 8,048,002 B2 | 11/2011 | Ghajar |
|---|---|---|
| 2004/0044293 A1 | 3/2004 | Burton |

(Continued)

FOREIGN PATENT DOCUMENTS

WO WO2015116832 8/2015

OTHER PUBLICATIONS

International Search Report and Written Opinion issued in PCT/US17/63029 dated Feb. 6, 2018.

*Primary Examiner* — Michael W Kahelin
(74) *Attorney, Agent, or Firm* — Workman Nydegger

(57) ABSTRACT

Embodiments are directed to identifying and measuring bodily states and feedback systems. A computer system initializes a tracking and measuring device to generate patient data related to a bodily state or feedback system of a patient. The computer system gathers the patient data using the initialized tracking and measuring device, and identifies a baseline parameter used to determine a baseline state relative to the gathered patient data. The computer system further gathers additional patient data using the initialized tracking and measuring device and compares the additional gathered patient data to the identified baseline parameter. Then, if the additional gathered patient data differs from the baseline state by a specified threshold amount, the computer system determines that a change in the patient's bodily state or feedback system has occurred and/or determines the amount of change in the bodily state or feedback systems that has occurred.

20 Claims, 10 Drawing Sheets

Related U.S. Application Data filed on Nov. 23, 2016, provisional application No. 62/425,874, filed on Nov. 23, 2016.

(51) Int. Cl.

| | |
|---|---|
| *A61B 5/00* | (2006.01) |
| *A61B 5/11* | (2006.01) |
| *G08B 21/00* | (2006.01) |
| *G08B 21/04* | (2006.01) |
| *A61B 5/01* | (2006.01) |
| *A61B 5/0205* | (2006.01) |
| *A61B 5/024* | (2006.01) |
| *G08B 21/06* | (2006.01) |
| *G08B 25/08* | (2006.01) |
| *A61B 5/08* | (2006.01) |
| *A61B 5/318* | (2021.01) |
| *A61B 5/369* | (2021.01) |

(52) U.S. Cl.
CPC ........... *A61B 5/1114* (2013.01); *A61B 5/1123* (2013.01); *A61B 5/165* (2013.01); *A61B 5/486* (2013.01); *A61B 5/4824* (2013.01); *A61B 5/7264* (2013.01); *A61B 5/7275* (2013.01); *G08B 21/00* (2013.01); *G08B 21/0476* (2013.01); *A61B 5/01* (2013.01); *A61B 5/02055* (2013.01); *A61B 5/02405* (2013.01); *A61B 5/08* (2013.01); *A61B 5/1107* (2013.01); *A61B 5/318* (2021.01); *A61B 5/369* (2021.01); *A61B 5/7282* (2013.01); *A61B 2503/12* (2013.01); *G08B 21/0438* (2013.01); *G08B 21/06* (2013.01); *G08B 25/08* (2013.01)

(58) Field of Classification Search
CPC ..... A61B 5/4824; A61B 5/486; A61B 5/7264; A61B 5/7275; A61B 5/01; A61B 5/02055; A61B 5/02405; A61B 5/0402; A61B 5/0476; A61B 5/08; A61B 5/1107; A61B 5/7282; A61B 2503/12; G08B 21/00; G08B 21/0476; G08B 21/0438; G08B 21/06; G08B 21/08

See application file for complete search history.

(56) References Cited

U.S. PATENT DOCUMENTS

| | | |
|---|---|---|
| 2007/0016096 A1 | 1/2007 | McNabb |
| 2009/0082641 A1 | 3/2009 | Giftakas |
| 2013/0012790 A1 | 1/2013 | Horseman |
| 2015/0051508 A1* | 2/2015 | Ghajar ................... A61B 5/163 600/558 |
| 2016/0022193 A1* | 1/2016 | Rau ......................... A61B 5/165 600/301 |
| 2016/0262608 A1* | 9/2016 | Krueger ................ G06T 19/006 |
| 2016/0262685 A1* | 9/2016 | Wagner ................ A61B 5/1123 |

\* cited by examiner

IDENTIFYING AND MEASURING BODILY STATES AND FEEDBACK SYSTEMS

BACKGROUND

The experience of pain is a complex physiological and psychological phenomenon. No known biomarker exists which can be used to directly measure pain. Most of the methodologies for measuring pain rely on patient reporting. The most popular methodologies include the Visual Analog Scale (VAS) and the Numeric Rating Scale (NRS). Because these techniques rely on feedback from the patient, they have natural limitations. Research has shown that these scales suffer from subjectivity and inconsistency/non-repeatability. Moreover, they are not practical for recording moment-to-moment changes in pain. They are particularly impractical for real-time pain tracking, such as during a period of physical or mental activity. Because of these limitations, there has been a tremendous demand within the healthcare community for pain measurement methods, which are not solely reliant on patient self-reporting.

In certain cases, pupillometry may be used to measure pain. Pupillometry is the measurement of pupil diameter. For example, various researchers have studied the use of pupillometry for pain measurement with children. These researchers have demonstrated the use of pupillometry to measure pain levels under various lighting conditions. Other researchers have shown, however, that there are many limitations for the use of pupillometry. For example, when a patient is in a post-anesthesia phase, the patient's pupils may still be impacted by the effects of drugs used during surgery and therefore not be a good indication of patient pain.

Eyelid movement may also be used to measure pain. During pain or distress, a subject may exhibit specific types of eyelid movement. For example, the subject may be prone to squinting or closing of the eyes during pain spikes. There may also be a potential for the use of startle eye blinks in measurement of pain, although research indicates that startle eye blinks can be affected by changes in the sensory environment, as startle eye blink is the body's natural defensive response to a sudden or threatening stimulus.

Body movement may also be used to measure changes in perceived pain. Researchers have characterized and established a correlation between pain and physical, cognitive and psychosocial function. However, prior research is limited because it is not able to create a pain measurement scale that repeatable and/or generalizable to an entire population, and thus could be standardized and validated. Moreover, it fails to provide for a mechanical or digital method by which the testing of body movement could be repeated and measured in a cost-effective, standardized way. Thus, creating a pain (or anxiety) measurement tool was not deemed practical.

Researchers have further shown a link between a decay in performance and pain. For example, one test case showed that a subject's ability to respond to sound stimuli declined with pain. However, the challenge with these historical methodologies for tracking pain is the great variance in task performance between subjects and the multitude of other factors that can influence performance (e.g., patient interest, fatigue, mental health, disease, age, ability, etc.).

Overall, there is current lack of reliable measures or indicators of pain outside of patient reporting, and this subjective modality of pain measurement can vary too widely between individuals or time points within the same individual to be reliably used for diagnostic purposes. Further, research into performance decay, body movements and/or eye behaviors as indicators of pain have not proven fruitful, and there remains a need for systems and methods for identifying and measuring, bodily states and feedback systems, such as pain and anxiety.

BRIEF SUMMARY

Embodiments described herein are directed to identifying and measuring bodily states and feedback systems. These bodily states may include emotional states such as happy, anxious, fearful, etc., biological states such as hungry, anemic, tired, etc., health states such as feverish, infected, well, etc., or other types of bodily states, including states which are a mixture of physical and emotional or psychological, such as pain. The feedback systems may include organismal responses of a status or change in a bodily state, which may include heat detection systems, pain detection systems, threat detection systems and other types of feedback systems. The embodiments described herein can identify these bodily states and can determine the operation or state of feedback systems. Although specific implementations for tracking eye movement, body movement and task performance are described herein, it will be understood that these principles, devices and systems may be applied to identify and measure substantially any aspect related to the functioning of the human (or animal) body.

Tracking various dynamics of movements related to the eyes can be used as a real-time, or close to real-time, pain (or anxiety) tracking, which does not solely rely on patient self-reporting. The embodiments described herein include a method, system and a software platform designed to measure human (or animal) pain and anxiety (or other states or systems) based on the subject's (i.e., the patient's) eye-related data: pupillometry, eyelid movement and eye movements. The systems herein can be in the form of a software application, software code, application, or video game (or similar electronic means) that can be implemented on any computer or similar computational device (e.g., PC, laptop, tablet, smartphone, server, virtual reality/augmented reality device). Embodiments track eye movements (including saccadic and micro saccadic movement), pupillometry and eyelid movement to measure pain or anxiety.

In some embodiments, the systems herein use algorithms to determine certain parameters of the eye data, which relate to different levels of pain (anxiety) and compare these to a set of reference baselines for determining levels of pain (anxiety).

In one embodiment, a system uses a series of rules or algorithms to interpret eye dynamics to determine if the eye dynamics correspond to pain and/or to different levels of pain.

In another embodiment, the system uses a series of rules or algorithms to interpret a subject's eye dynamics to determine if the eye dynamics correspond to anxiety and/or to different levels of anxiety.

Further embodiments describe a method, system and a software platform designed to measure human (or animal) pain and anxiety based on the subject's body movements. The system can be in the form of a software application, software code, application, or video game (or similar electronic means) that can be implemented on any computer or similar computational device (e.g., PC, laptop, tablet, smartphone, server, virtual reality/augmented reality device). The invention tracks body movements to measure pain or anxiety.

In one embodiment, the system uses a series of rules or algorithms to interpret a subject's various body movements, including stops, pauses, jitters, shaking and fractional or fractionated movements to determine certain parameters of the movement data, which relate to different levels of pain (anxiety) and compare these to a set of reference baselines for determining levels of pain (anxiety).

In one embodiment, a system uses a series of rules or algorithms to interpret movement dynamics to determine if the movement dynamics correspond to pain and/or to different levels of pain.

In another embodiment, the system uses a series of rules or algorithms to interpret a subject's movement data and movement dynamics to determine if the body movements correspond to anxiety and/or to different levels of anxiety.

Still further embodiments describe a method, system and a software platform designed to measure human (or animal) pain and anxiety based on a measured decay in the subject's performance. The system can be in the form of a software application, software code, application, or video game (or similar electronic means) that can be implemented on any computer or similar computational device (e.g., PC, laptop, tablet, smartphone, server, virtual reality/augmented reality device). The invention tracks the decay in performance of a task or tasks.

The system provides the user with a given set of tasks to be performed in a computer-generated environment or a virtual or augmented environment. The environment can have two (i.e., 2-D) or more dimensions. Various parameters of one or more tasks, called performance dynamics, are identified and evaluated. The performance dynamics are compared to a baseline, which determines whether the performance dynamics indicate a change in pain (anxiety) and/or different levels and/or an amount of pain (anxiety).

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages will be set forth in the description which follows, and in part will be apparent to one of ordinary skill in the art from the description, or may be learned by the practice of the teachings herein. Features and advantages of embodiments described herein may be realized and obtained by means of the instruments and combinations particularly pointed out in the appended claims. Features of the embodiments described herein will become more fully apparent from the following description and appended claims.

BRIEF DESCRIPTION OF THE DRAWINGS

To further clarify the above and other features of the embodiments described herein, a more particular description will be rendered by reference to the appended drawings. It is appreciated that these drawings depict only examples of the embodiments described herein and are therefore not to be considered limiting of its scope. The embodiments will be described and explained with additional specificity and detail through the use of the accompanying drawings in which.

DETAILED DESCRIPTION

Figure 1:
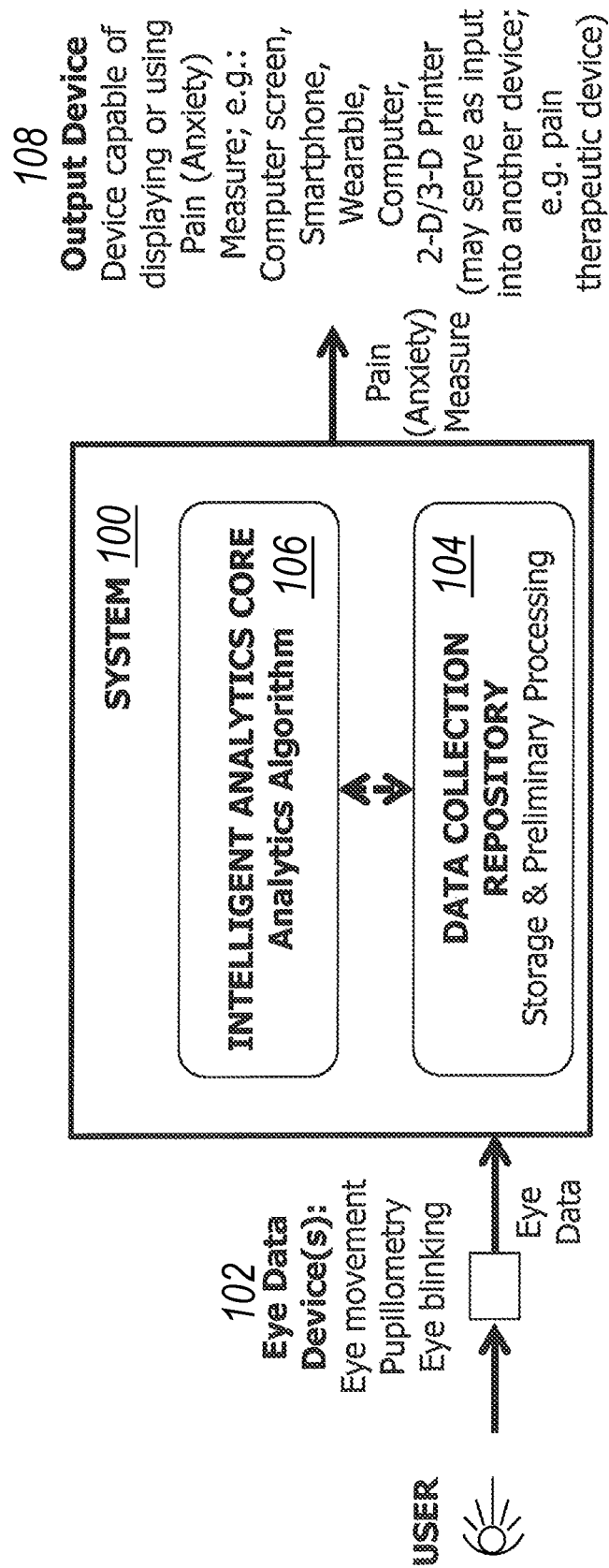
FIG. 1 illustrates a system overview in which embodiments described herein may operate.

As noted above, the embodiments described herein are generally directed to identifying and determining bodily states and feedback systems. In one embodiment, a computer system initializes a tracking and measuring device to generate patient data related to a bodily state or feedback system of a patient. The computer system gathers the patient data over a period of time using the initialized tracking and measuring device, and identifies a baseline parameter used to determine a baseline state relative to the gathered patient data. The computer system further gathers additional patient data over a second period of time using the initialized tracking and measuring device and compares the additional gathered patient data to the identified baseline parameter. Then, if the additional gathered patient data differs from the baseline state by a specified threshold amount, the computer system determines that a change in the patient's bodily state or feedback system has occurred. The computer system may additionally determine an amount of change in the patient's bodily state or feedback system that has occurred.

The embodiments described herein may implement various types of computing systems. These computing systems are now increasingly taking a wide variety of forms. Computing systems may, for example, be mobile phones, electronic appliances, laptop computers, tablet computers, wearable devices, desktop computers, mainframes, and the like. As used herein, the term "computing system" includes any device, system, or combination thereof that includes at least one processor, and a physical and tangible computer-readable memory capable of having thereon computer-executable instructions that are executable by the processor. A computing system may be distributed over a network environment and may include multiple constituent computing systems (e.g., a cloud computing environment). In a cloud computing environment, program modules may be located in both local and remote memory storage devices.

As described herein, a computing system may also contain communication channels that allow the computing system to communicate with other message processors over a wired or wireless network. Such communication channels may include hardware-based receivers, transmitters or transceivers, which are configured to receive data, transmit data or perform both. Embodiments described herein also include physical computer-readable media for carrying or storing computer-executable instructions and/or data structures. Such computer-readable media can be any available physical media that can be accessed by a general-purpose or special-purpose computing system.

Still further, system architectures described herein can include a plurality of independent components that each contribute to the functionality of the system as a whole. This modularity allows for increased flexibility when approaching issues of platform scalability and, to this end, provides a variety of advantages. System complexity and growth can be managed more easily through the use of smaller-scale parts with limited functional scope. Platform fault tolerance is enhanced through the use of these loosely coupled modules. Individual components can be grown incrementally as business needs dictate. Modular development also translates to decreased time to market for new functionality. New functionality can be added or subtracted without impacting the core system.

The embodiments described herein are designed to overcome at least some of the limitations of prior pain measurement and/or anxiety methods by creating a method, system and a software platform that is capable of measuring pain without sole reliance on patient self-report, and does so in a low cost, standardized, repeatable way. In fact, the subject need not be aware that bodily state measurements are taking place. Moreover, bodily state or feedback system measurements can be taken during activities. As used herein, the term "bodily state" may refer to a biological state, an emotional state, a health state or some other state of a subject's (or patient's) body. The term "feedback system" may indicate any of a patient's bodily feedback systems that provide information to the brain including pain information. Although many of the embodiments described herein refer to detecting a patient's pain level or anxiety level, it will be understood that the methods and systems herein can be used to detect, monitor and measure substantially any bodily state or body feedback system.

At least some of the embodiments herein are further differentiated from prior solutions in that they do not rely singly on any one of the three common eye data methods: pupillometry, eye movement or eye blinking. Rather, the embodiments combine these data streams and then determine and select key data parameters specific to tracking pain or anxiety. By combining the data streams, determining, and selecting key data parameters specific to tracking pain or anxiety—as described herein—the present invention enables a more consistent and reliable measure of a patient's pain (or anxiety).

Further, implementation of the specific set of rules applied within the disclosed and claimed methods and systems enable a solution to a long-felt need in the pain industry. A patient's pain (or anxiety) can be characterized and communicated as an objective measure without reliance upon subjective patient self-reporting, and as a result, more personalized and effective treatment regimens can be developed and implemented.

Additionally, by determining and selecting key data parameters specific to tracking pain or anxiety, as disclosed herein, the disclosed systems and methods can beneficially identify early cues of patient pain (e.g., the onset or even before the onset of pain) and prophylactic treatment regimens can be initiated to decrease the intensity of the pain and/or the duration of the pain, and in some instances, prophylactic treatment may eliminate any perception of pain. Such embodiments, particularly where paired with wearable devices such as augmented or virtual reality eyeglasses, can beneficially enable patients that experience chronic or episodic pain to curb the intensity and/or the duration of pain. Such implementations can measurably increase the patient's quality of life.

FIG. 1 shows an overview of one embodiment of the system. The embodiment takes eye movements (which can include, for example, saccadic and micro saccadic movement but may also generally include facial expressions centered on the eye such as squinting, wincing or furrowing of the eyebrow), pupillometry, and eyelid movement (collectively referred to as "eye data" herein) from one or more eye data devices (102). Eye data devices gather eye movement data from one or more of eye or gaze tracking, eyelid movement tracking, face movement tracking and/or pupillometry sensors or mechanisms. Examples of such dye data devices include, without limitation, eye-attached lenses, optical tracking devices, electric potential measurement devices, or electromyography (EMG) devices. However, the present invention is not restricted to the current state of these eye data device technologies.

Eye data may include numerous data types, such as blink frequency, squint frequency, fixations, saccades/micro-saccades, intersaccadic drift velocities, saccadic/micro-saccadic velocity/angular velocity or acceleration, scan paths, smooth pursuit motion, eye/gaze angle, pupillary diameter (PD), pupillary light reflex amplitude (PLRA, the difference between PD before and after light stimulation), eye blinking frequency, velocity/acceleration and duration. Eye data may be collected from one or both eyes of a patient.

Referring again to FIG. 1, system 100 collects the raw eye data from one or more eye data devices (102) into a data collection repository (104), and performs basic processes such as time synchronization and data storage.

Referring again to FIG. 1, the prepared eye data is processed in the intelligent analytics core (106) of the invention. The intelligent analytics core evaluates multiple eye data parameters (e.g., "eye dynamics") and has the capability to compare these to a baseline of eye dynamics or feedback systems. This baseline may include different representative levels of the eye dynamics for given levels/measurements of pain, anxiety or other bodily states or feedback systems. If the parameters differ from the baseline by a (changeable) threshold amount, the algorithms of the intelligent analytics core will determine if a change (or an amount of change) in the subject's level of pain (anxiety) has occurred. The intelligent analytics core then formats this pain (anxiety) level information into one or more formats that can be interpreted by one or more output devices (108). An output device can be one of a variety of device types, including, without limitation, a PC monitor, wearable device, smartphone, 2-D or 3-D printer, etc. The output device may also be another computer (e.g., health data repository at a hospital) or a piece of medical equipment, such as an opioid dosage device.

Eye dynamics do not need to be a single set of eye data, but may be a set of various eye data, which in combination may be important for measuring pain or anxiety. Examples of eye dynamics may, without limitation, include various combinations such as the following: pupil acceleration from one visual stimuli to another, intersaccadic drift velocity between distinct visual cues related to an action (e.g., before shooting a gun in a video game), or average rate of eye blinking per time interval during an activity (e.g., target acquisition in a video game).

The baseline may be established by preset parameters. It may also be established by multiple analyses of the same patient (subject) or other patients (subjects) during various levels of pain (anxiety), and/or in various physical or psychological activities or states. Algorithms may be implemented to interpret eye data and eye dynamics to determine which correspond or correlate to perception of pain (anxiety) versus other causes.

Figure 2:
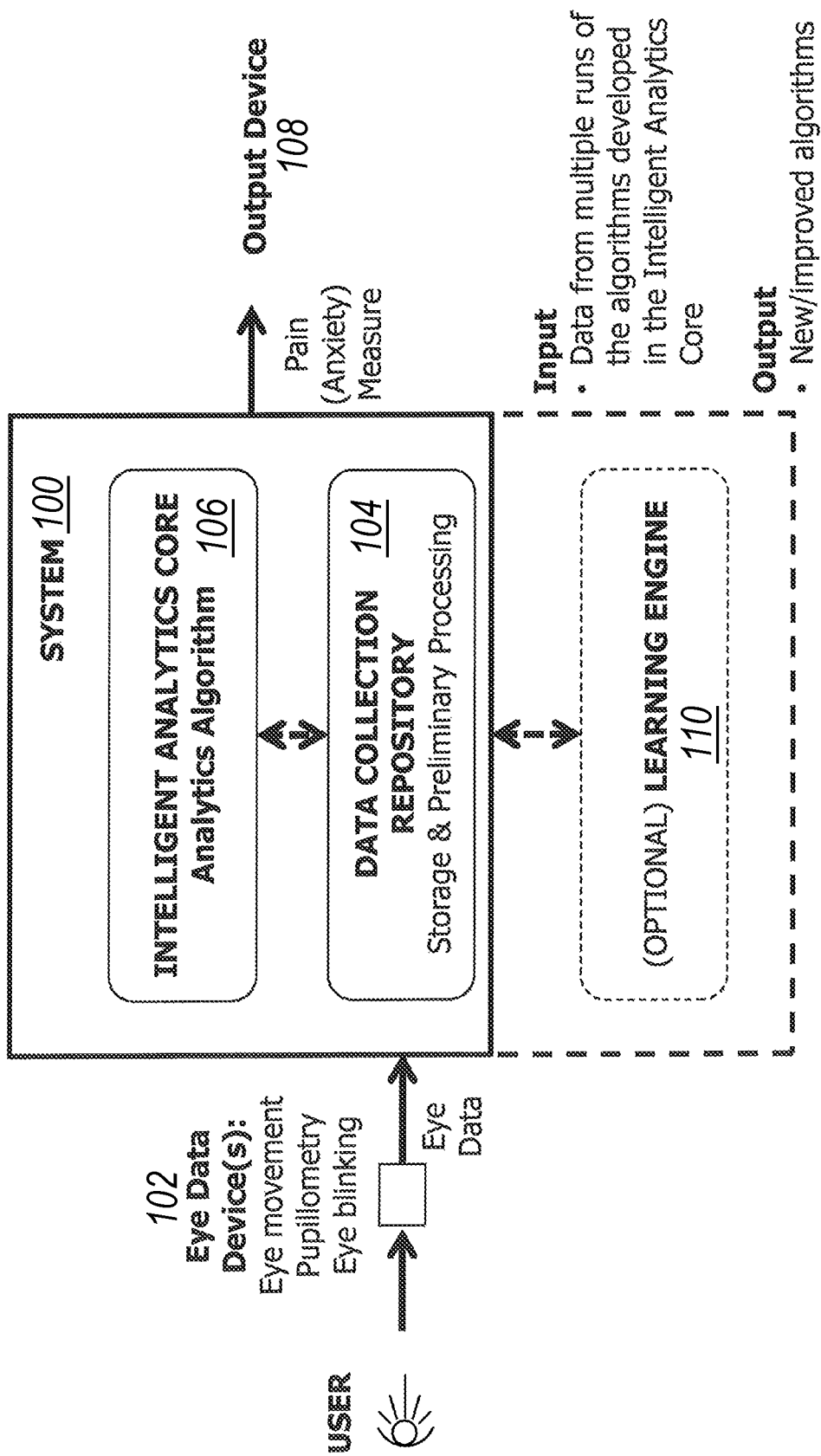
FIG. 2 illustrates a system overview with an optional learning engine.

In another embodiment of the invention, as shown in FIG. 2, the system incorporates a learning engine (110). This learning engine has the ability to learn, over multiple iterations of the system, so as to improve the accuracy, precision or predictive capability of the intelligent analytics core (106). The learning engine can consist of a variety of analytics tools, including, without limitation, big data analytics, deep learning algorithms, neural networks, multivariate statistical tools or various other statistical tools.

Figure 3:
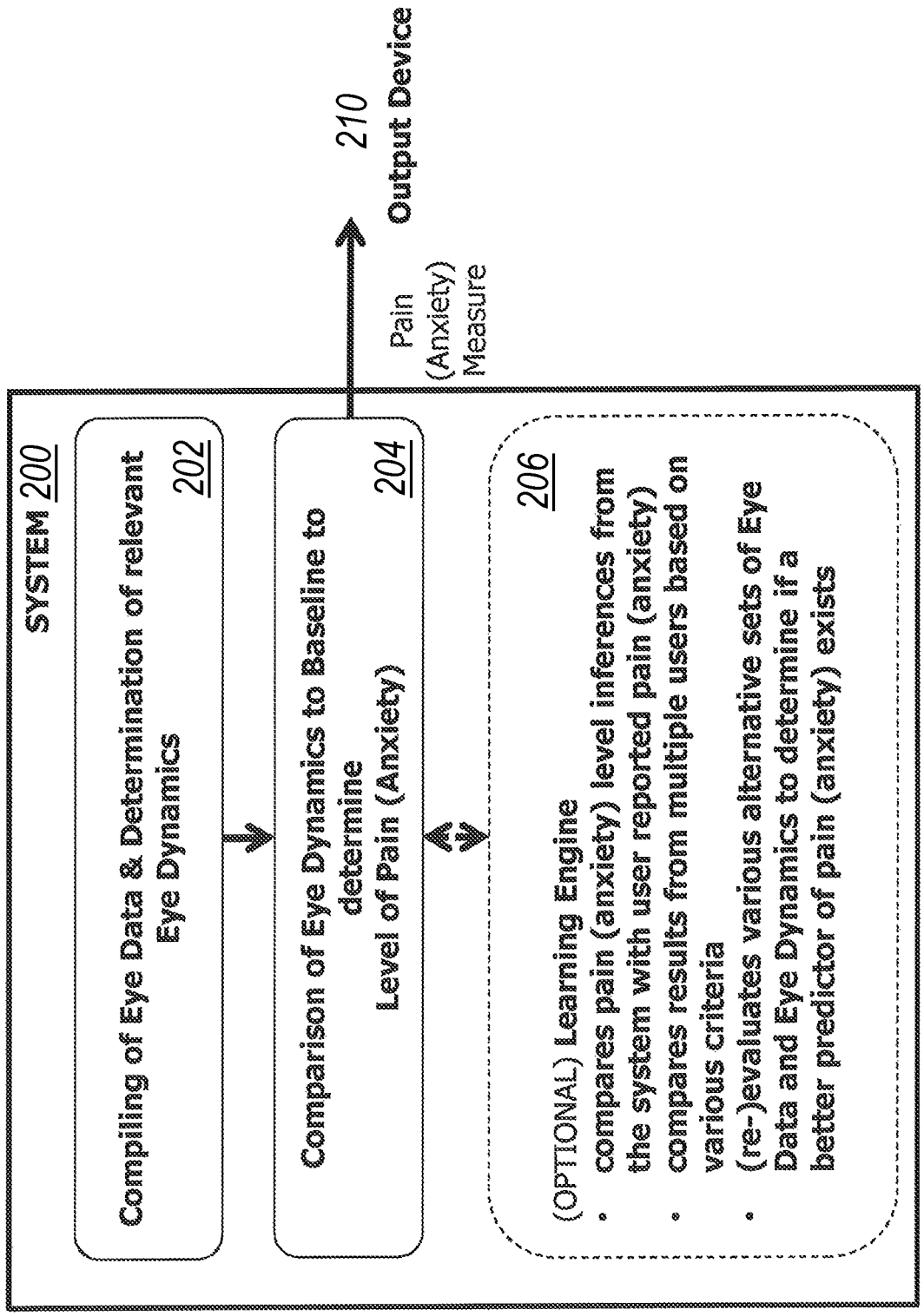
FIG. 3 illustrates an example process overview that uses eye, eyelid or pupil movement or changes to identify bodily state changes or changes in feedback systems.

FIG. 3 shows one embodiment of the process flow of the system (200). In step 202, eye data collected from the eye data device is compiled (e.g., signals from various eye data devices are time synchronized), and the eye data is then analyzed to determine the key eye dynamics the system will evaluate. In step 204 the eye dynamics are compared against the baseline, which provides parameters/criteria for determining different levels of pain or anxiety.

Continuing with FIG. 3, step 206 is an optional step, which exists in those embodiments of the invention which include the learning engine. In step 206 the learning engine uses various techniques to reevaluate the performance of the algorithms of the intelligent analytics core. In this step, various analyses are completed, including, without limitation, reevaluating the data points which were used in the eye dynamics to determine if different eye data would provide a more precise, predictive and/or efficient determinant of different levels of pain (anxiety).

The algorithms for evaluating the eye dynamics are reevaluated, the baseline ranges are reevaluated, user input on their actual perceived pain (anxiety) is compared to the level of pain inferred or predicted by the intelligent analytics core, and the data from multiple users is compared to the data from a single user, based on various psycho-social parameters (e.g., gender, age, economic status, etc.)

In some embodiments, embodiments include filters in the intelligent analytics core or the data collection repository which eliminate data that are not applicable to pain (anxiety) measurement. For example, the subject may exhibit unusual saccadic eye movement while playing an exciting video game. Data filters will be applied to certain data points to reduce the probability of misinterpretation of the raw data. In some embodiments, the learning engine may re-evaluate these filters to improve the efficiency for isolating dynamics related to pain (anxiety).

In one embodiment, the system may be combined with a source of visual stimulus, such as a video game or software, which entices the subject's eye(s) to move in a prescribed pattern (e.g., following a ball appearing and disappearing in a sinusoidal pattern in space). The system records the subject's eye data and eye dynamics during various levels of pain (anxiety) to create a baseline and algorithm to estimate future pain (anxiety) levels in other circumstances while playing the video game. The video game or software would then become part of the system, because it would allow for a controlled environment which would make it easier to control and predict eye dynamics. The system would also make it easier to determine potential causes for certain eye dynamics and to exclude eye dynamics which might look like an indication of pain, but are in fact not relevant. The algorithms developed with the use of such a video game/software may become so predictive that they can be used without the video game/software in an uncontrolled (general life) setting.

In another embodiment, the system may be combined with a method which tracks the activity of the subject. For example, a method may be provided which tracks what the subject is looking at to provide context for the potential psychological and physiological state of the subject. This method may also track the performance of the subject while engaging in the activity. For example, an analytics tool may be provided which tracks a subject's performance while playing a video game or a sport.

As used herein, the term "performance" includes any of motor or cognitive performance when performing a task and can be measured on an individual basis (e.g., comparing performance of an individual between time points) or on an aggregate basis (e.g., comparing individual performance to other individuals' performance, individually or collectively). It should be appreciated that a task can be any action performed by the individual. This can include routine tasks or prescribed tasks and encompasses any task that involves motor skills, cognitive skills, or a combination of motor and cognitive skills to accomplish. It should further be appreciated that an action does not require movement or activity; it can be stillness or even sleep.

In some embodiments, the disclosed systems measure and/or track an individual's performance through one or more tasks, and based on the individual's performance, the system can identify baseline identifiers and parameters for any of a given number or type of bodily states and feedback systems. Subsequent measures of the individual's performance through routine or prescribed tasks can be used to refine baseline identifiers and/or parameters, to define homeostatic variations in bodily states and feedback systems, and/or to create thresholds within a bodily state or feedback system (e.g., a comparative measure or amount of pain). These data may be specific to an individual or to clusters of individuals or they may be applicable to a global population. It should be appreciated that some applications of the disclosed systems and methods may, therefore, be valuable and applicable on an individual-by-individual basis and can provide a predictive and accurate model of the individual's bodily state (e.g., provide a personalized pain model) even if the data cannot be generalized to a population-level model.

In some embodiments, the systems disclosed herein utilize responses from biofeedback systems to provide context to various performance metrics. For example, an elevated heart rate can be indicative of an individual experiencing an intense episode of anxiety, but it is also associated with exercise. Information from biofeedback systems can provide the context necessary to decipher changes in an individual's performance, and these data can provide valuable cross-validation measures, which enable the system to associate certain performance metrics (or combinations of performance metrics) with a given bodily state and/or feedback systems.

In some embodiments, the system can identify the degree of change in the bodily state or feedback systems experienced by the individual (e.g., the pain intensity). These data can be used to extrapolate or determine treatments to return the individual to a desired or baseline bodily state, to affect or interrupt feedback systems, or to prevent an increase in the amount of change occurring in the bodily state and/or feedback systems. For example, the system can identify an increase in the individual's amount of pain and can correlate the amount of pain the individual is experiencing with a prescribed amount of pain medication or a treatment regimen that would stop the pain from increasing, decrease the amount of pain, or return the individual to a pain-free or baseline level of pain.

Accordingly, in some embodiments, the system is combined with an analgesic mechanism (e.g., an opioid drip, a spinal stimulator, etc.), which controls the amount of analgesic therapeutic being delivered to the subject. The amount of analgesic therapeutic delivered to the subject can be based, for example, on the comparative change in the subject's pain. It should be appreciated that in some embodiments, the amount of pain may be perceived differently by different individuals and may, therefore, correspond to different perceived amounts of pain. A small change in a bodily state may require a larger amount of analgesic or a more thorough treatment regimen in a first individual, but that same amount of change experienced by another individual may require a lower amount of analgesic or a less thorough treatment regimen to achieve the same effect. In some such embodiments the amount of analgesic (pain therapy) may be controllable by a healthcare provider or automatically limited to avoid overdose or harm to the patient. Measuring the amount of analgesic the subject receives could also be valuable input to validating the pain level predicted by the intelligent analytics core.

In another embodiment, the system is combined with analgesic mechanisms (e.g., opioid drip, spinal stimulator, virtual reality pain distraction game, etc.) to control the analgesic mechanism and dispense the analgesic according to the patient's determined level of pain.

In another embodiment, the system may be combined with one or more biofeedback devices (e.g., heart rate variability monitor, galvanic skin response monitor, electroencephalogram/EEG, fMRI, breath sensor) which may, for example, provide other data to evaluate whether eye dynamics, movement data/dynamics information or other performance metrics correspond to pain or other causes.

In another embodiment, the system may be integrated into a pair of glasses worn by the subject. This could be in the form of regular eye glass frames, an augmented reality device, or a virtual reality device (e.g., virtual reality head mounted display). This would allow the system to be used by the subject for extended periods of time.

Other embodiments are directed to measuring pain or other bodily states using a method, system and a software platform, which is capable of measuring pain without solely relying on subject (patient) self-reporting. In fact, the subject need not be aware that pain (anxiety) measurements are taking place. Moreover, pain measurements can be taken during activities.

Figure 4:
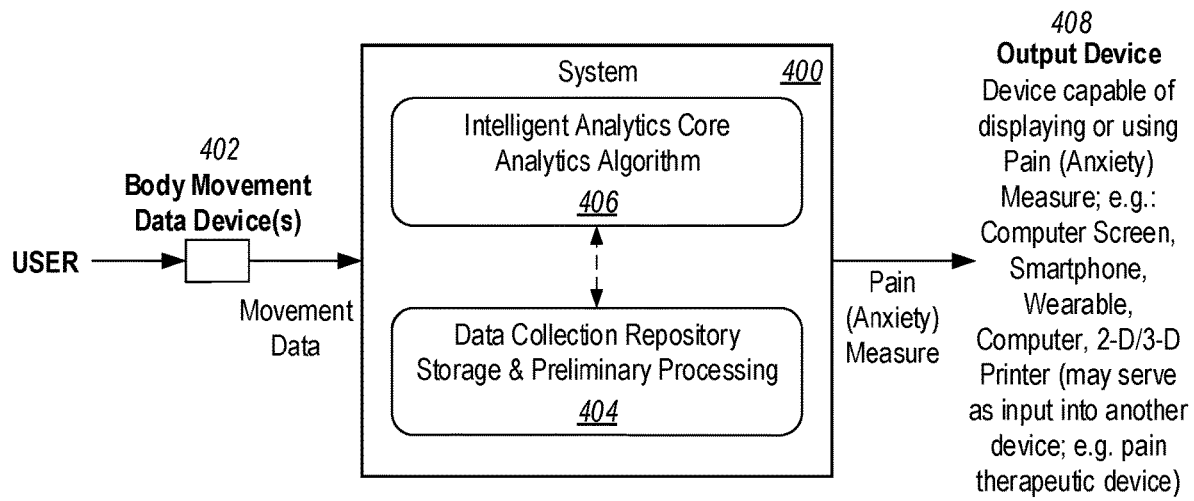
FIG. 4 illustrates an alternative system overview in which embodiments described herein may operate.

FIG. 4 shows an overview of one embodiment of the system. The invention takes body movement data or "movement data" from one or more body movement data devices (401). Body movement data devices gather movement data from all or part of the body. Examples of such devices include, without limitation, virtual reality head-mounted displays and hand/body motion trackers, augmented reality head-mounted displays, laser body motion sensors, infrared motion sensors, light camera motion sensors or electromagnetic body motion sensors. It should be noted, however, that the embodiments herein are not restricted to the current state of these body movement data device technologies.

Movement data may include numerous parameters, such as range of limb (head, neck, torso, etc.) movement, angular velocity or acceleration of limb (head, neck, torso, etc.) movement, movement paths, smooth pursuit motion, fractional or fractionated movements, reflex motion, force or momentum of a movement (e.g., impact force of a punch), and movement (performance) decay.

Referring again to FIG. 4, system 400 collects the raw movement data from one or more body movement data devices (402) into a data collection repository (404), and performs basic processes such as time synchronization and data storage.

In FIG. 4, the prepared movement data is processed in the intelligent analytics core (406). The intelligent analytics core evaluates multiple movement data parameters ("movement dynamics") and has the capability to compare these to a baseline of movement dynamics. The baseline may include different representative levels of the movement dynamics for given levels/measurements of pain (anxiety). If the movement dynamics differ from the baseline by a (changeable) threshold amount, the algorithms of the intelligent analytics core will determine if a change (or an amount of change) in the subject's level of pain has occurred. The intelligent analytics core then formats this pain (anxiety) level information into one or more formats that can be interpreted by one or more output devices (408). An output device can be one of a variety of types, including, without limitation, a PC monitor, wearable device, smartphone, 2-D or 3-D printer, etc. The output device may also be another computer (e.g., health data repository at a hospital) or a piece of medical equipment, such as an opioid dosage device.

Movement dynamics do not need to be a single set of movement data, but may be a set of various movement data, which in combination may be used for measuring pain or anxiety. Examples of movement dynamics may, without limitation, include various combinations such as the following: limb acceleration from one task to another, path smoothness between distinct points of movement related to a task (e.g., before shooting a gun at different targets in a video game), or average speed of movement between points in a task (e.g., different targets in a video game).

The baseline may be established by preset parameters. It may also be established by multiple analyses of the same subject or other subjects during various levels of pain (anxiety), and/or in various physical or psychological activities or states. The invention includes algorithms, which interpret movement data and movement dynamics to determine which correspond/correlate to perception of pain (anxiety) versus other causes.

Figure 5:
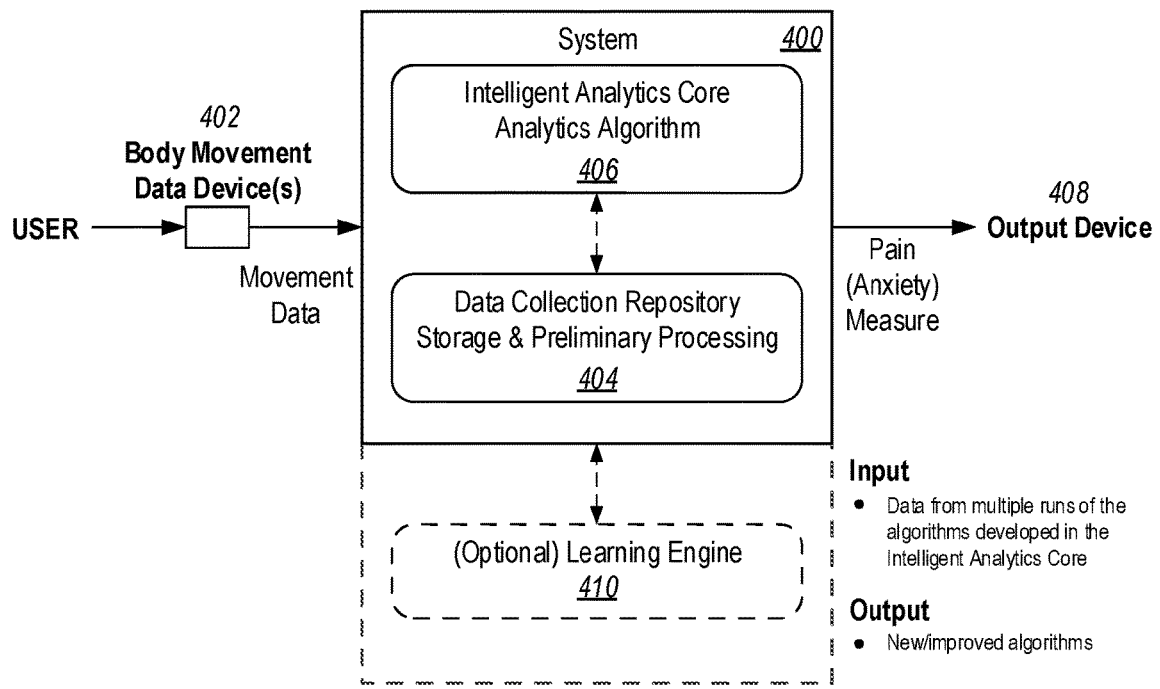
FIG. 5 illustrates a system overview with an optional learning engine.

In one embodiment, as generally shown in FIG. 5, the system adds a learning engine (410) to the system. This learning engine has the ability to learn, over multiple iterations of the system, so as to improve the accuracy, precision or predictive capability of the intelligent analytics core (406). The learning engine can consist of a variety of analytics tools, including, without limitation, big data analytics, deep learning algorithms, neural networks, multivariate statistical tools or various other statistical tools.

Figure 6:
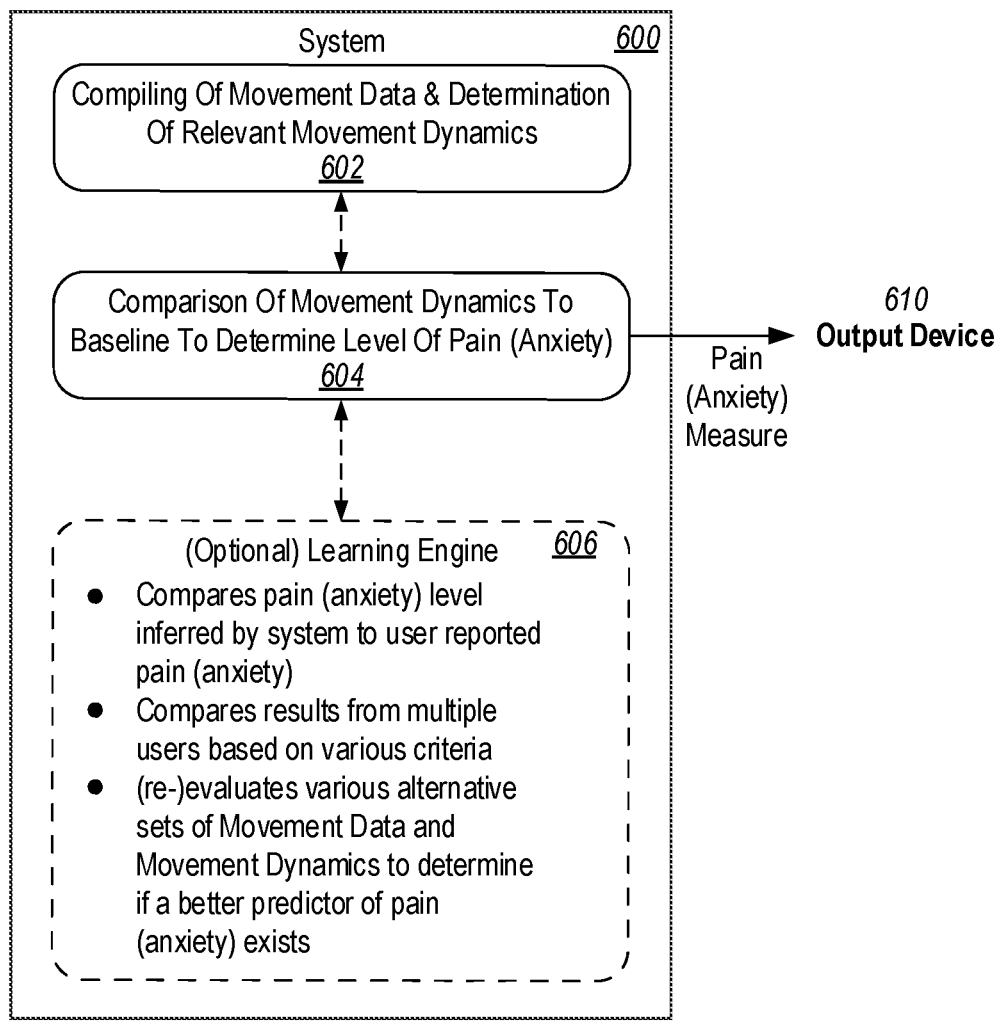
FIG. 6 illustrates an example process overview that uses body movement to identify bodily state changes or changes in feedback systems.

FIG. 6 shows a process flow of the system 600 in an exemplary embodiment. In step 602, movement data collected from the body movement data device is compiled (e.g., signals from various body movement data devices is time synchronized), and the movement data is then analyzed to determine the key movement dynamics the system will evaluate. In step 604 the movement dynamics are compared against the baseline, which provides parameters/criteria for determining different levels of pain (anxiety). The determined pain (anxiety) measurement is output to one or more output devices 610.

Continuing with FIG. 6, step 606 is an optional step, which exists in those embodiments of the invention which include the learning engine. In step 606 the learning engine uses various techniques to reevaluate the performance the algorithms of the intelligent analytics core. In this step, various analyses are completed, including, without limitation: reevaluating data points which were used in the movement dynamics to determine if different movement data would provide a more precise, predictive and/or efficient determinant of different levels of pain (anxiety).

The algorithms for evaluating the movement dynamics are re-evaluated, the baseline ranges are re-evaluated, user input on their actual perceived pain (anxiety) is compared to the level of pain inferred/predicted by the intelligent analytics core, and the data from multiple users is compared to the data from a single user, based on various psycho-social parameters (e.g., gender, age, economic status, etc.)

In some embodiments, filters may be implemented which eliminate data that are not applicable to pain (anxiety) measurement. For example, the subject may exhibit unusual body movement while playing an exciting video game. Data filters will be applied to certain data points to reduce the probability of misinterpretation of the raw data and validate whether the unusual body movement actually corresponds to pain (anxiety).

In one embodiment, the system may be combined with a source of tasks, such as a virtual reality (VR) video game/application, which entices the subject to move in a prescribed pattern (e.g., following a ball moving in a sinusoidal pattern in space). The system records the subject's movement data and movement dynamics during various levels of pain (anxiety) to create a baseline and algorithm to estimate future pain (anxiety) levels in other circumstances while playing the VR video game/application. The VR video game/application would then become part of the system, because it would allow for a controlled environment, which would make it easier to control and predict movement dynamics; it would also be easier to determine potential causes for movement dynamics and to exclude movement dynamics which might look like an indication of pain, but are in fact not relevant. The algorithms developed with the use of such a video game/application may become so predictive that they can be used without the video game/application in an uncontrolled (general life) setting.

In another embodiment, the system is combined with an analgesic mechanism (e.g., opioid drip, spinal stimulator, etc.), which controls the amount of analgesic therapeutic being delivered to the subject. Measuring the amount of analgesic the subject uses could be valuable input to validating the pain level predicted by the intelligent analytics core. In some embodiments, the system may be combined with analgesic mechanisms (e.g., opioid drip, spinal stimulator, virtual reality pain distraction game, etc.) to actually control the analgesic mechanism.

In another embodiment, the system may be combined with one or more biofeedback devices (e.g., heart rate/heart rate variability monitor, galvanic skin response monitor, electroencephalogram/EEG, fMRI, etc.) which may, for example, provide other data to evaluate whether movement dynamics correspond to pain or other causes.

In another embodiment, the system may be integrated into a pair of glasses worn by the subject. This could be in the form of regular eye glass frames, an augmented reality device, or a virtual reality device (e.g., virtual reality head mounted display). This would allow the system to be used by the subject for extended periods of time.

Figure 7:
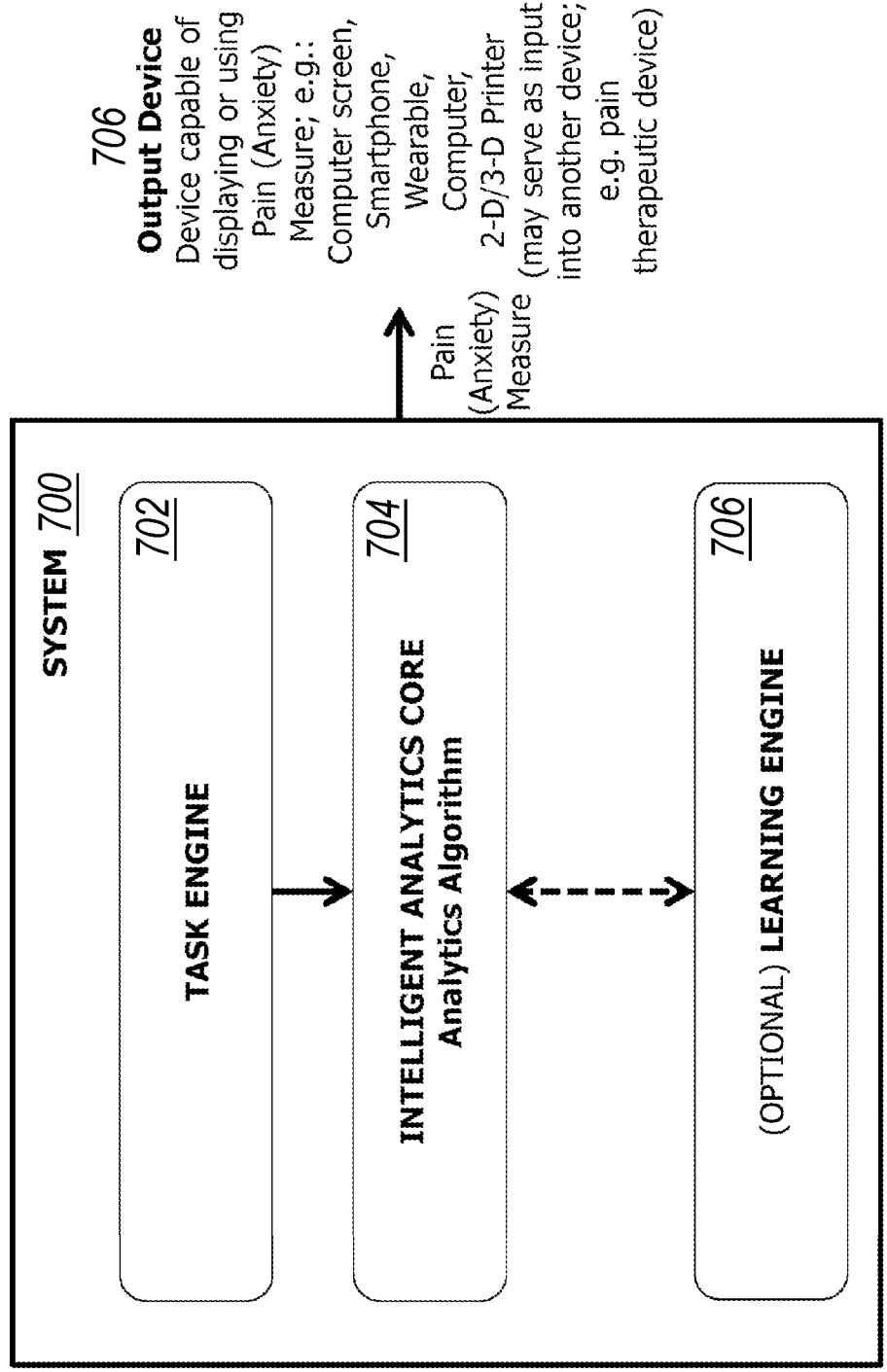
FIG. 7 illustrates an alternative system overview in which embodiments described herein may operate.

FIG. 7 shows an overview of one embodiment of the system. The invention provides a task engine (702). The task engine creates a digital model of various tasks which the user can perform. Examples of tasks include, without limitation, shooting at targets, collecting objects in a virtual environment, driving a virtual car in a video game, performing math calculations, solving puzzles, etc.

In one embodiment, the user is given a set of tasks in the form of a video game. The user is not aware of which of many tasks relates to measures of pain (anxiety). Referring to FIG. 7, the intelligent analytics core (704) tracks various parameters of one or more tasks, called performance dynamics. The intelligent analytics core identifies and evaluates performance along these performance dynamics.

Performance dynamics may include numerous parameters or combinations of parameters, such as level of activity in a virtual environment or game, number of targets acquired, target acquisition time, time between target acquisition and firing, idle time between target acquisition, firing accuracy, number of targets hit as a percentage of available targets, time and accuracy in solving a puzzle, etc.

Referring again to FIG. 7, the intelligent analytics core (704) evaluates multiple performance dynamics and has the capability to compare these to a baseline of performance dynamics. The baseline may include different representative levels of the performance dynamics for given levels/measurements of pain (anxiety). If the parameters differ from the baseline by a (changeable) threshold amount, the algorithms of the intelligent analytics core will determine if a change (or an amount of change) in the subject's level of pain has occurred. The intelligent analytics core then formats this pain (anxiety) level information into formats that can be interpreted by output devices (706).

An output device can be one of a variety of types, including, without limitation, a PC monitor, wearable device, smartphone, 2-D or 3-D printer, etc. The output device may also be another computer (e.g., a health data repository at a hospital) or a piece of medical equipment, such as an opioid dosage device.

Performance dynamics do not need to be a single type of performance, but may be a set of various performance data, which in combination may be important for measuring pain or anxiety. The baseline may be established by preset parameters. It may also be established by multiple analyses of the same user or other users during various levels of pain (anxiety), and/or in various physical or psychological activities or states. Embodiments also include algorithms, which interpret performance data and performance dynamics to determine which correspond or correlate to perception of pain (anxiety).

In one embodiment, as generally shown in FIG. 7, the system 700 further differentiates itself from prior art by adding a learning engine (708) to the system. This learning engine has the ability to learn, over multiple iterations of the system, so as to improve the accuracy, precision or predictive capability of the intelligent analytics core (704). The learning engine can consist of a variety of analytics tools, including, without limitation, big data analytics, deep learning algorithms, neural networks, multivariate statistical tools or various other statistical tools.

Figure 8:
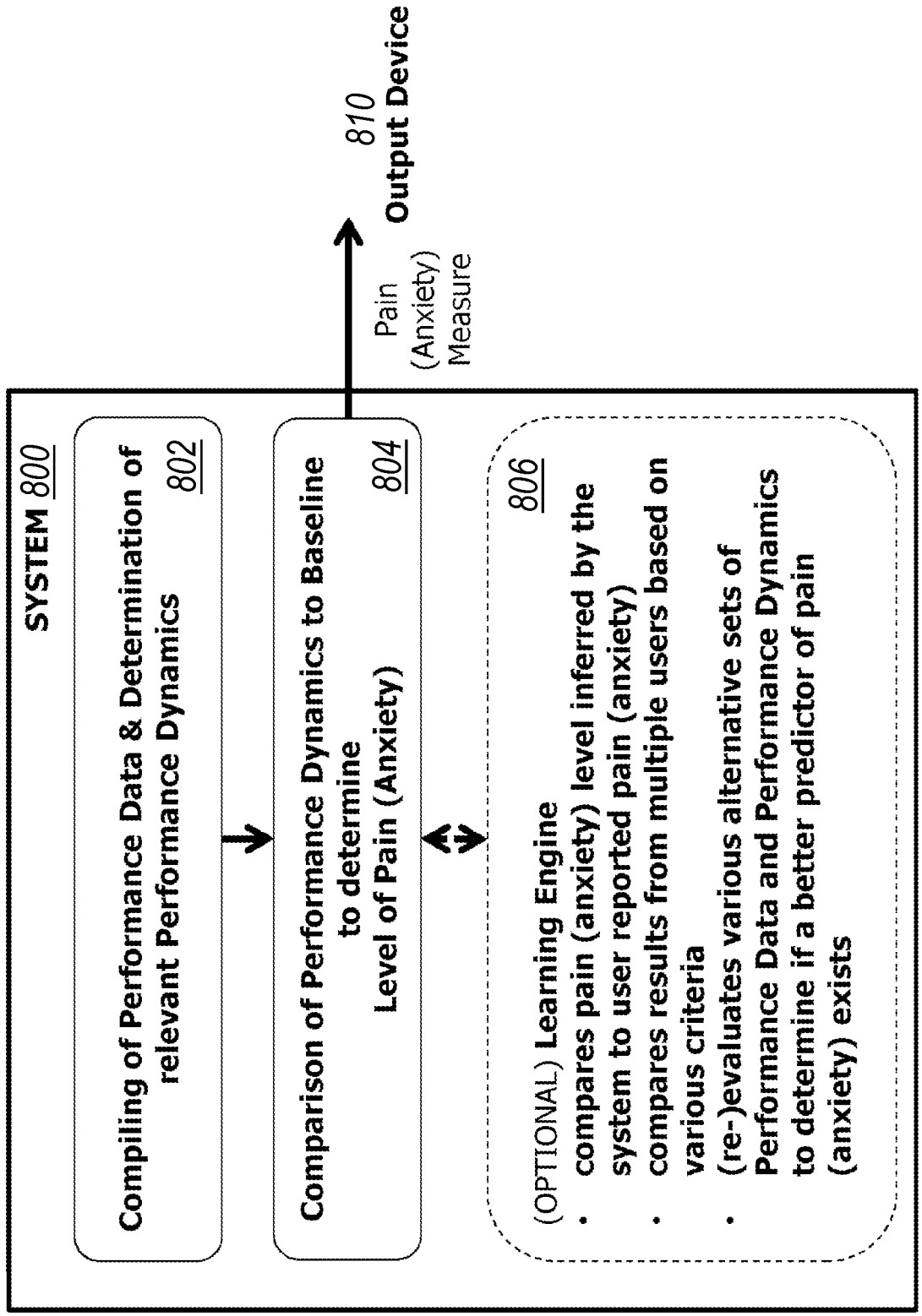
FIG. 8 illustrates an example process overview that uses performance decay to identify bodily changes or changes in feedback systems.

FIG. 8 shows the process flow of the system (800) in an exemplary embodiment. In step 802, performance data collected by the intelligent analytics core is compiled, and the performance data is then analyzed to determine the key performance dynamics the system will evaluate. In step 804 the performance dynamics are compared against the baseline, which provides parameters/criteria for determining different levels of pain (anxiety). The determined pain (anxiety) measurement is output to one or more output devices 810.

Continuing with FIG. 8, step 806 is an optional step, which exists in those embodiments of the invention which include the learning engine. In step 806 the learning engine uses various techniques to reevaluate the performance algorithms of the intelligent analytics core. In this step, various analyses are completed, including, without limitation: data points which were used in the performance dynamics are reevaluated to determine if different performance data would provide a more precise, predictive and/or efficient determinant of different levels of pain (anxiety), the algorithms for evaluating the performance dynamics are reevaluated, the baseline ranges are re-evaluated, user input on their actual perceived pain (anxiety) is compared to the level of pain inferred/predicted by the intelligent analytics core, or the data from multiple users is compared to the data from a single user, based on various psycho-social parameters (e.g., gender, age, economic status, etc.).

In some embodiments, filters may be implemented which eliminate data that are not applicable to pain (anxiety) measurement. For example, the subject may exhibit unusual performance decay while playing a challenging or exceptionally difficult game level in a video game. Data filters may be applied to certain data points to reduce the probability of misinterpretation of the raw data and to corroborate that the performance decay is, indeed, related to pain (anxiety).

In one embodiment, the system may be combined with an analgesic mechanism (e.g., opioid drip, spinal stimulator, etc.), which controls the amount of analgesic therapeutic being delivered to the subject. Measuring the amount of analgesic the subject uses may be used as input to validate the pain level predicted by the intelligent analytics core.

In another embodiment, the system may be combined with analgesic mechanisms (e.g., opioid drip, spinal stimulator, virtual reality pain distraction game, etc.) to actually control the analgesic mechanism. In still another embodiment, the system may be combined with one or more biofeedback devices (e.g., heart rate/heart rate variability monitor, galvanic skin response monitor, electroencephalogram/EEG, fMRI, etc.) which may, for example, provide other data to evaluate whether performance dynamics information correspond to pain or other causes.

Accordingly, the systems described herein can further enable the translation of performance metrics into a prescription for management or treatment of bodily states (e.g., pain) and can additionally translate a patient's pain into a visual scale (e.g., a uniform visual analog scale) for use by healthcare providers in developing treatment regimens and/or prescribing therapeutics. Additionally, or alternatively, the systems disclosed herein can beneficially enable the calibration of treatment regimens or prescriptions in an individual-specific manner. In some instances, medications or other therapeutics can have a limited or reduced effect on the patient (or in some cases a hyperactive effect), and the performance metrics received and interpreted by the disclosed systems can help to identify such situations as well as provide actionable insights into how to better treat the individual. For example, an individual on a cocktail of prescription drugs may not respond to an additional therapeutic in the manner expected. The response may be weak, as indicated by an amount or degree of amelioration in performance decay, and the prescribed treatment can be increased or changed as a result to a therapy that is effective within the given individual—given the individual's specific state and situation.

Figure 9:
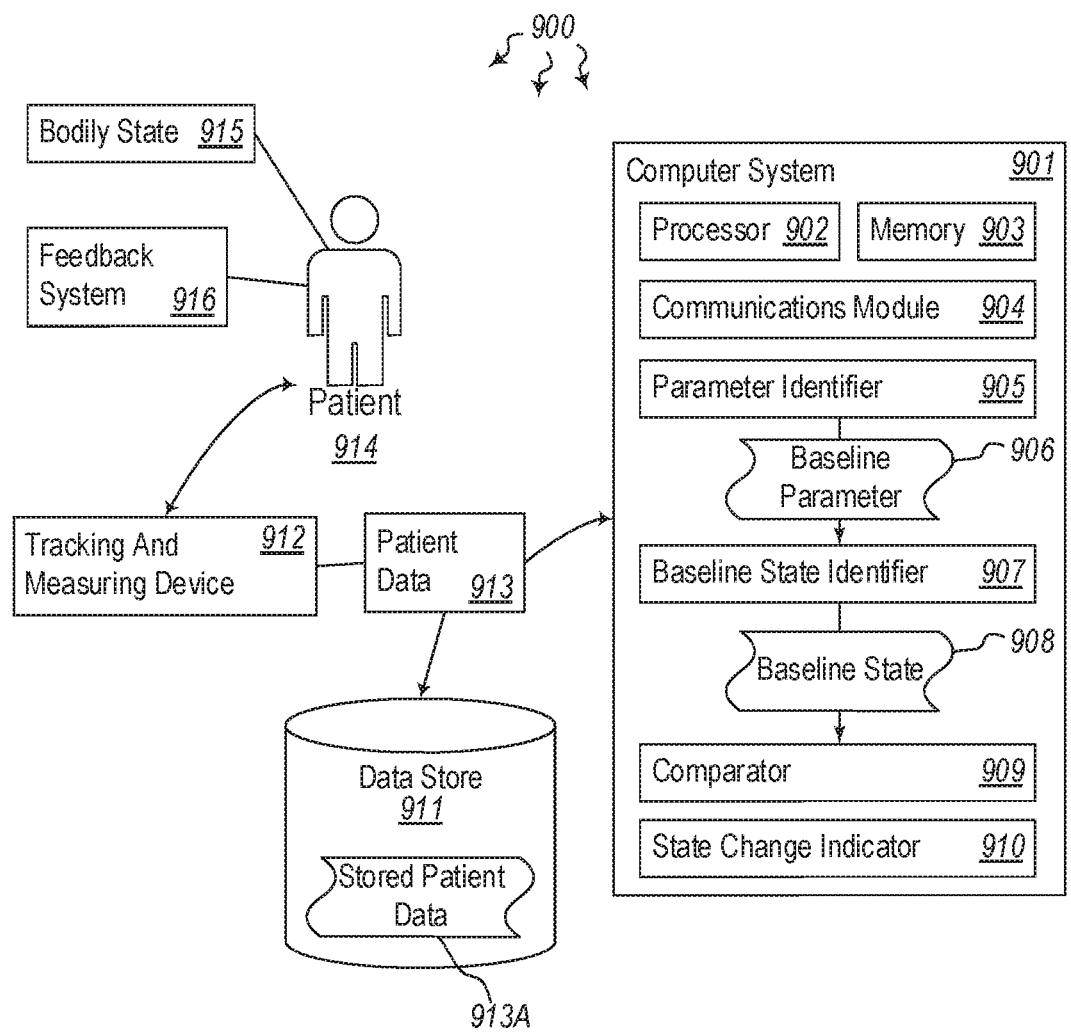
FIG. 9 illustrates a computer architecture in which embodiments described herein may operate including identifying and determining bodily states and feedback systems.

Turning now to FIG. 9, a computer architecture 900 is illustrated in which at least one embodiment described herein may be employed. The computer architecture 900 includes a computer system 901. The computer system 901 includes at least one processor 902 and at least some system memory 903. The computer system 901 may be any type of local or distributed computer system, including a cloud computer system. The computer system 901 includes modules for performing a variety of different functions. For instance, communications module 904 may be configured to communicate with other computer systems. The communications module 904 may include any wired or wireless communication means that can receive and/or transmit data to or from other computer systems. The communications module 904 may be configured to interact with databases, mobile computing devices (such as mobile phones or tablets), embedded or other types of computer systems. These concepts will be explained further below with regard to methods 1000, 1100 and 1200 of FIGS. 10, 11 and 12, respectively.

Figure 10:
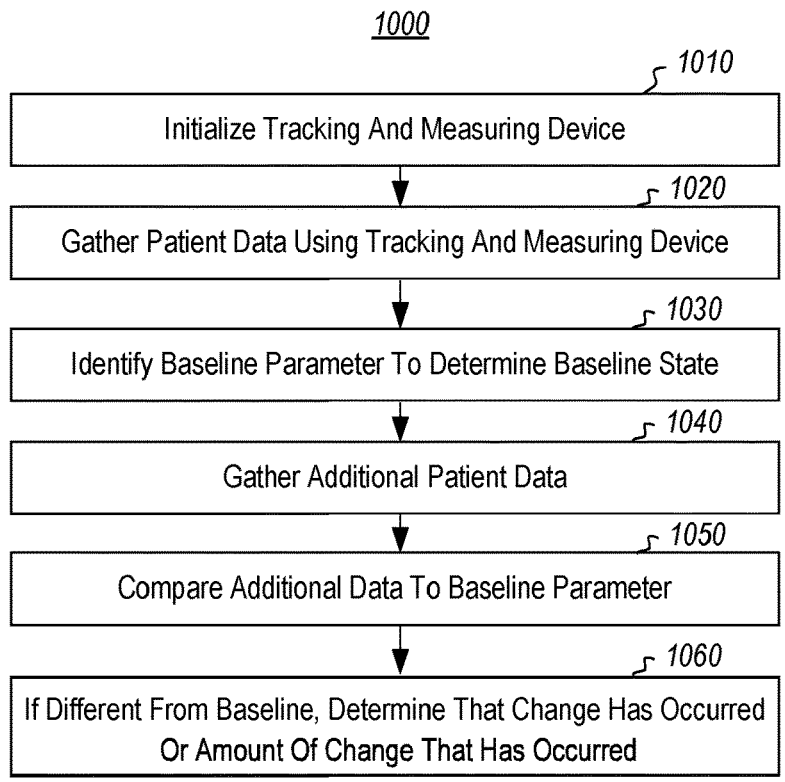
FIG. 10 illustrates an example method for identifying and determining bodily states and feedback systems.
Figure 11:
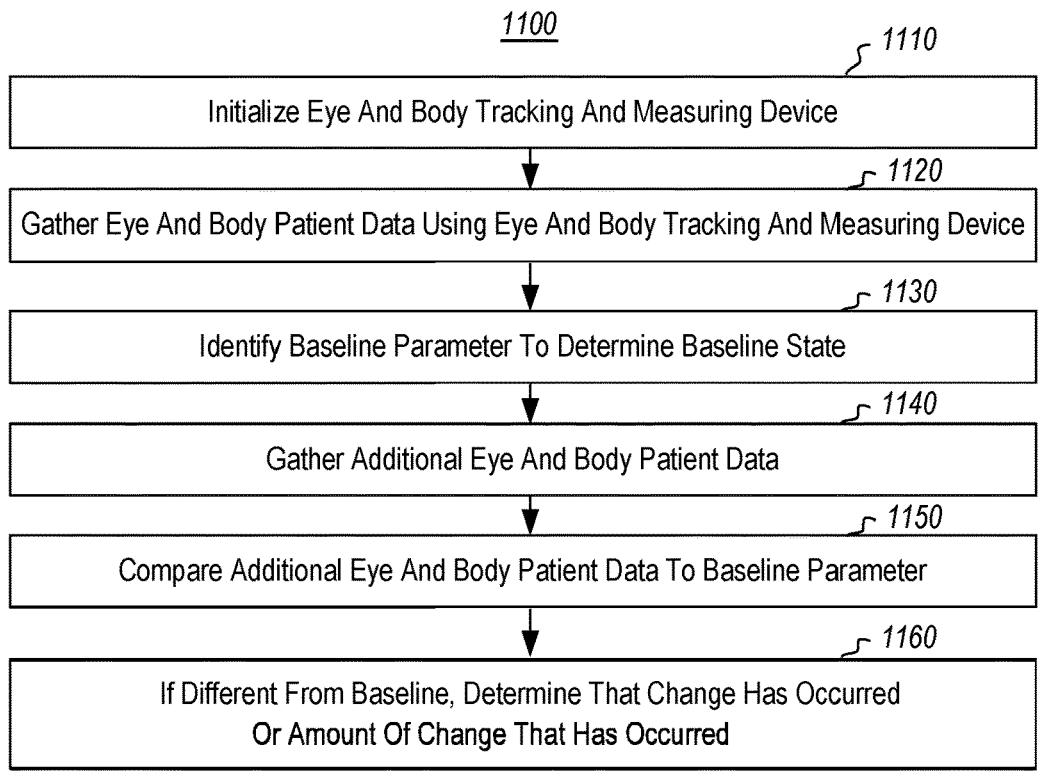
FIG. 11 illustrates an alternative example method for identifying and determining bodily states and feedback systems.
Figure 12:
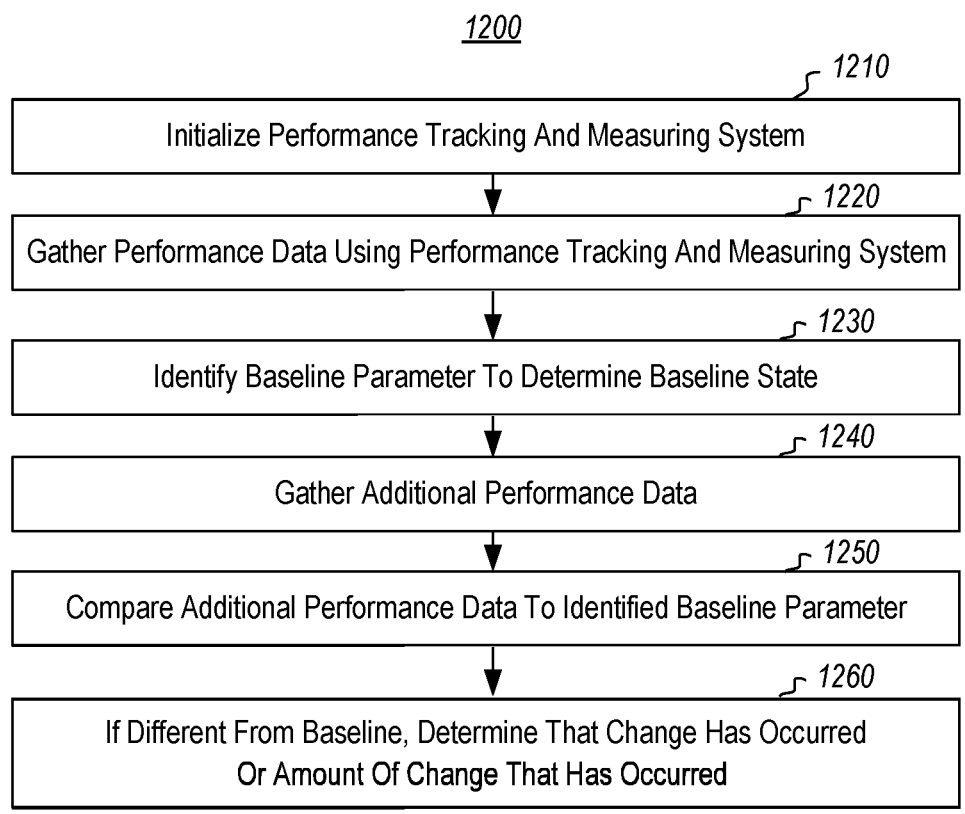
FIG. 12 illustrates an alternative example method for identifying and determining bodily states and feedback systems.

In view of the systems and architectures described above, methodologies that may be implemented in accordance with the disclosed subject matter will be better appreciated with reference to the flow charts of FIGS. 10, 11 and 12. For purposes of simplicity of explanation, the methodologies are shown and described as a series of blocks. However, it should be understood and appreciated that the claimed subject matter is not limited by the order of the blocks, as some blocks may occur in different orders and/or concurrently with other blocks from what is depicted and described herein. Moreover, not all illustrated blocks may be required to implement the methodologies described hereinafter.

FIG. 10 illustrates a flowchart of a method 1000 for identifying and measuring bodily states and feedback systems. The method 1000 will now be described with frequent reference to the components and data of environment 900.

In one embodiment, a computer system is provided that includes one or more processors and one or more computer-readable storage media having stored thereon computer-executable instructions that, when executed by the one or more processors, configure the computer system to create a multidimensional sensory environment for identifying and measuring bodily states and feedback systems by causing the computer system to perform various steps including those outlined below. The computer system (e.g., 901) includes processor 902 and memory 903, along with communications module 904. The communications module may comprise any number of radios including cellular radios, Wi-Fi radios, Bluetooth radios, global positioning system (GPS) radios or other radios. These transceiver radios may be configured to communicate with any number of devices on various communication networks.

The computer system 901 may be configured to initialize a tracking and measuring device 912 to generate patient data 913 related to a bodily state 915 or feedback system 916 of a patient 914 (step 1010). The tracking and measuring device 912 may be any type of computing system, gaming system, virtual or augmented reality system, or other mechanical or electromechanical apparatus designed to measure a patient's bodily state or feedback systems. As noted above, the patient's bodily state may refer to the patient's emotional state, physical state, health state or other bodily state. The patient's feedback systems may include the nervous system, which gathers sensory inputs and transmits them to the brain, the endocrine system which generates hormones in response to stimuli (e.g., testosterone in a fight or flight scenario), the circulatory system, the digestive system, the reproductive system or other bodily systems.

Thus, the tracking and measuring device 912 may gather patient data 913 (e.g., eye movement data, body movement data, etc.) over a period of time (step 1020) which infer or relate to these bodily states 915 or feedback systems 916. This patient data 913 may be sent to the computer system 901, to a data store 911 (whether local or remote) or to other specified locations for storage (resulting in stored patient data 913A). The data may be encrypted and de-identified (i.e., anonymized) so that it conforms to patient privacy laws. The computer system 901 may then identify at least one baseline parameter 906 used to determine a baseline state 908 relative to the gathered patient data. The parameter identifier 905 of computer system 901 identifies a baseline parameter 906 that forms a starting point or baseline measurement for one or more of the patient's bodily states or feedback systems (step 1030). This baseline parameter 906 may be adjusted over time, as the patient's body changes. Alternatively, the baseline parameter 906 may be based on a preset value determined from analyzing other patients. The baseline state identifier 907 uses the baseline parameter 906 to identify a baseline state 908 that is unique to the patient 914.

The computer system 901 gathers additional patient data over a second period of time using the initialized tracking and measuring device 912 (step 1040). The comparator 909 then compares the additional gathered patient data to the identified baseline parameter 906 (step 1050). In some cases, the additional patient data may be gathered continuously from the tracking and measuring device 912, or, in other cases, the additional patient data may be gathered at multiple instances over a specified time period. If the additional gathered patient data differs from the baseline state 908 by a specified threshold amount, the state change identifier 910 of the computer system 901 determines that a change in the patient's bodily state 915 or feedback system 916 has occurred (step 1060). In some embodiments, the determination that a change has occurred may additionally, or alternatively, include a determination of an amount of change that has occurred in the patient. It should be noted that the parameter identifier 905, the baseline state identifier 907, the comparator 909 and the state change identifier 910 may be implemented entirely or partially in software, hardware or firmware, or some combination thereof.

Additionally, it should be appreciated that any of the foregoing identifiers and/or parameters can be determined in a number of different ways. For example, an individual's baseline state identifier can be determined by measuring the individual's bodily states—or components of feedback systems associated therewith—over time and isolating one or a plurality of key identifiers that are indicative of the individual's baseline. Alternatively, an individual's baseline state identifier can be correlated with a global baseline state identifier determined through analytic analysis of populations of individual baseline state identifiers. The global baseline state identifier may be a single identifier for a given population or it may be any number of different baseline state identifiers associated with a plurality of clusters that identify a population. In instances where clusters have been identified, insights into measurements associated with an individual's bodily state or feedback systems can tie the individual to a given cluster—and thereby be associated with a cluster-specific baseline state identifier. In any of the foregoing exemplary embodiments, an identifier or parameter can be improved over time through application of collected data on the same or different individuals. It should be appreciated that as one or more of the identifiers or parameters become more predictive, it can improve the number or refinement in population clusters and/or improve the accuracy and predictive power associated with a global baseline identifier/parameter.

In some embodiments, the tracking and measuring device 912 is designed to determine a patient's pain level or anxiety level, or changes in these levels. The tracking and measuring device 912 may be an eye tracking and measuring device configured to track or measure eye movement, eyelid movement, pupillometry, or track other movements related to the eye. The eye tracking and measuring device may thus track and/or measure where the patient is looking, how long the patient is looking in any one direction, how often the patient's eyes move, how often the patient's eyelid moves, how fast the eyelid moves, how dilated the patient's pupils are, how the pupil dilation changes (e.g., pupillometry), etc. The eye tracking and measuring device may provide each type of eye, eyelid and pupillometry data separately, or may combine the different type of eye data to form a data stream that includes all eye-related information, or at least some combination of eye-related information.

Such a combined data stream may be used to form the baseline parameter 906. The baseline parameter may thus not rely singly on any one of the three above-mentioned eye data methods: pupillometry, eye movement or eye blinking. Rather, the computer system 902 combines these data streams and then determines and selects key data parameters specific to tracking pain, anxiety, or other bodily states. The patient data from the combined eye monitors may be time synchronized. This patient data (i.e., eye dynamics data) may include pupil acceleration from one visual stimulus to another or Intersaccadic drift velocity between distinct visual cues related to an action. Such eye dynamics data may be captured before shooting a gun in a video game, or may be determined during target acquisition in a video game. Precise moments for identifying movement may be synchronized between the visual stimulus (e.g., a video game) and the tracking and measuring device 912.

Indeed, the computer system 901 may include or may be communicatively connected to a source of visual stimulus that entices the patient's eyes to move in a prescribed pattern. If the patient does not move his or her eyes in the prescribed pattern, or is slow to respond, or makes other irregular movements, these may be identified and recorded. These visual stimuli may be used when gathering patient data 913 and determining a baseline parameter 906. The computer system 901 may also be configured to implement and/or derive an algorithm to estimate future pain (anxiety) levels in other circumstances while responding to the visual stimulus. In some cases, tracking what the patient is currently looking at may provide context for a psychological or physiological state of the patient. If the patient is heavily sedated, for example, the patient's eyes may move in a slower manner, the pupils may be dilated, and the patient may have trouble following a moving target. If the patient is highly anxious, contrasting behavior may be observed by the eye tracking and measuring device.

In some embodiments, the patient's eye movements or body movement, or other aspects of the patient's eye or body is recorded and stored as a video file. The stored data can be re-evaluated (e.g., by one or more components of system 700, like the learning engine 706 and/or the intelligent analytics core 704) to increase the predictive power and accuracy of the disclosed methods on an individual-by-individual basis or at a population level. This can advantageously provide historic data that can be analyzed after-the-fact without requiring additional data to be retrieved from a particular patient and can further enable more powerful analytic analysis and subsequent identification of key identifiers and/or parameters. For example, new or updated models can be tested and/or trained using the recorded video files, expediting model validation and/or implementation.

In other embodiments, the tracking and measuring device 912 is a body movement tracking and measuring device configured to track or measure one or more portions of the patient's body. The body movement tracking and measuring device can use 2D or 3D scans, infrared sensors, electromagnetic sensors, light camera, video data or other movement trackers to identify when and how much a patient is moving. Some body movements may be indicative of a certain bodily state such as pain or anxiety. These body movements may be measured to determine not only the patient's current bodily state, but also the magnitude or intensity of that state. The tracking and measuring device 912 may be configured to establish a baseline state 908 for body movement based on one or more baseline parameters 906. Differences between a patient's current movements and the baseline state are analyzed to identify whether they are sufficiently different from the baseline state (i.e., whether they surpass a movement dynamics threshold).

The tracking and measuring device 912 may output many different types of data, some of which may be unneeded or unwanted data. The computer system 901 may be configured to filter and exclude those patient data that appear relevant to a given bodily state or feedback system, but are actually not relevant thereto. The computer system may implement a learning engine (e.g., 110 of FIG. 1 or 410 in FIG. 4) that, over time, learns which patient data are most relevant, and which can be filtered and discarded. The learning engine may also be configured to learn, over multiple iterations, how to improve the accuracy, precision or predictive capability of the computer system 901, by evaluating performance of the steps that were performed. Each of the steps may be performed again (using the same data or different data), in order to identify those data that are useful and pertinent to determining a patient's bodily state, and those that are unnecessary.

Still further, in some embodiments the computer system 901 may be connected to one or more output devices (e.g., 108 of FIG. 1). The output devices may be configured to display or use the bodily state data. The computer system 901 may format the data for each of these output devices prior to sending the data. In some cases, the output device may comprise a multidimensional sensory environment that allows the patient to visualize the identified and measured bodily states or feedback systems. For instance, if the computer system 901 determines that the patient is experiencing pain, the multidimensional sensory environment (e.g., virtual reality or augmented reality) may allow the patient to view his or her body and show a pain source, or show a level of pain coming from various areas of the body. Areas in pain may be color coded for easier identification. Using such an environment, a physician, nurse or caregiver may be able to better understand what a patient is feeling, and where his or her current pain source exists.

The computer system may be combined with an analgesic mechanism that controls the amount of analgesic therapeutic being delivered to the patient (e.g., an opioid drip, a spinal stimulator, etc.). Thus, a patient's detected pain or anxiety level may directly control the analgesic mechanism, releasing more or less of the analgesic according to the determined pain/anxiety level. This level of control may, of course, be tempered by a physician, allowing the physician to reduce the level of analgesic when necessary (i.e., overriding the determination to dispense more of the drug). Furthermore, limits on drug dosage may be entered into the computer system or analgesic mechanism to prevent the patient from receiving more of the analgesic than is necessary.

FIG. 11 illustrates a flowchart of a method 1100 for identifying and measuring bodily states and feedback systems. The method 1100 will now be described with frequent reference to the components and data of environment 900 of FIG. 9.

Method 1100 describes a method, implemented at a computer system that includes at least one processor, for identifying and measuring bodily states and feedback systems. The method includes initializing an eye and body tracking and measuring device (e.g., 912) to generate eye and body patient data related to a bodily state 915 or feedback system 916 of a patient 914 (step 1110). The eye and body patient data 913 indicates eye movements, eyelid movements, pupillometry changes, or body movements over a period of time. The method 1100 next includes gathering the eye and body patient data 913 using the initialized eye and body tracking and measuring device 912 (step 1120). This data may be gathered using a single device, or multiple devices. The gathered data may be analyzed or stored as a combined stream of data, or may be analyzed and stored as separate data streams.

Method 1100 further includes identifying at least one baseline parameter 906 used to determine a baseline state 908 relative to the gathered eye and body patient data 913 (step 1130), and gathering additional eye and body patient data over a second period of time using the initialized eye and body tracking and measuring device (step 1140). The method 1100 then includes comparing the additional gathered eye and body patient data to the identified baseline parameter 906 (step 1150), and, if the additional gathered eye and body patient data differs from the baseline state 908 by a specified threshold amount, determining that a change in the patient's bodily state 915 or feedback system 916 has occurred (step 1160). In some embodiments, the determination that a change has occurred may additionally, or alternatively, include a determination of an amount of change that has occurred in the patient.

In some embodiments, eye-related data is combined into a single data stream. Thus, eye movement data, eyelid movement data and pupillometry data are all combined into a data stream and used, in combination, to determine a patient's current bodily state. The computer system on which the method 1100 is performed may be combined with or communicatively connected to various biofeedback devices that provide an additional stream of data related to the patient. Such biofeedback devices may include pulse detectors, respiration detectors, body temperature detectors, or other similar devices. Additionally, or alternatively, the computer system may be integrated into or communicatively connected to a pair of eye glasses, to an augmented reality device, or to a virtual reality device worn or used by the patient. Each of these devices and systems may have its own corresponding data formats and protocols. As such, the data streams may be formatted into a specified format interpretable by that device or system.

FIG. 12 illustrates a flowchart of a method 1200 for identifying and measuring bodily states and feedback systems. The method 1200 will now be described with frequent reference to the components and data of environment 900 of FIG. 9.

The method 1200 is implemented at a computer system that includes at least one processor. The method includes initializing a performance tracking and measuring system (e.g., 912) to generate performance data (e.g., 913) related to a patient's performance of a task (step 1210). The method then gathers the performance data over a period of time using the initialized performance tracking and measuring system (step 1220), and identifies at least one baseline parameter 906 used to determine a baseline state 908 relative to the gathered performance data (step 1230). The performance data indicates how the patient 914 is performing a given task (e.g., performing a turn in a driving video game).

The method 1200 then gathers additional performance data over a second period of time using the initialized performance tracking and measuring device (step 1240), and compares the additional gathered performance data to the identified baseline parameter 906 (step 1250). If the additional gathered performance data differs from the baseline state by a specified threshold amount, method 1200 determines that a change in the patient's bodily state or feedback system has occurred (step 1260). This determination may also include an indication of the amount of change that occurred in the patient. As such, the patient's bodily states and feedback systems may be monitored and measured for indications of pain, anxiety or other states.

A learning engine may be implemented to analyze the gathered performance data and the determined change in the patient's bodily state 915 or feedback system 916 to improve accuracy and precision in selecting baseline parameters establishing the baseline state. The learning engine may be further configured to receive and consider patient inputs indicating a current bodily state. For instance, the patient 914 may provide his or her own indication of current bodily state. This user indication may affect the baseline parameter 906 and/or the baseline state 908. Adjusting the baseline parameter or state to be more in line with the user's current indication of bodily state will increase the accuracy of the system in determining the user's overall physical state.

As with the embodiments described above, the computer system performing the method 1200 may be connected to an analgesic mechanism that controls an amount of analgesic therapeutic being delivered to the patient. The amount of analgesic therapeutic delivered to the patient may be based on determined changes in the patient's bodily state or feedback system over time. Limits or controls may be placed on the patient's ability to self-medicate in this manner.

Accordingly, methods, systems and computer program products are provided which identify and measure bodily states and feedback systems. The concepts and features described herein may be embodied in other specific forms without departing from their spirit or descriptive characteristics. The described embodiments are to be considered in all respects only as illustrative and not restrictive. The scope of the disclosure is, therefore, indicated by the appended claims rather than by the foregoing description. All changes which come within the meaning and range of equivalency of the claims are to be embraced within their scope.

The invention claimed is:

1. A system for determining a level and/or an amount of pain in a user based on limb movement dynamics, the system comprising:
   a limb movement tracking and measuring device; and
   a computer system communicatively coupled to the limb movement tracking and measuring device, wherein the computer system comprises:
   one or more processors; and
   one or more computer-readable storage media having stored thereon computer-executable instructions that, when executed by the one or more processors, configure the computer system to identify and measure pain by causing the computer system to perform at least the following:
   monitor a limb movement task using data received from the limb movement tracking and measuring device;
   calculate movement dynamics of limb movement during the limb movement task using the limb movement tracking and measuring device, the movement dynamics comprising:
   a path smoothness between distinct points of limb movement related to the limb movement task; and
   a speed of task performance, wherein the speed of task performance comprises measures of limb acceleration within the limb movement task or a duration of task performance;
   compare the calculated movement dynamics with a baseline parameter; and
   determine a level and/or an amount of pain based on the comparison of the movement dynamics with the baseline parameter.

2. The computer system of claim 1, wherein the computer system is integrated into an augmented reality or virtual reality system, and wherein the limb movement tracking and measuring device is a component of the augmented reality or virtual reality system.

3. The computer system of claim 1, wherein the limb movement tracking and measuring device comprises at least one of: a virtual reality head-mounted display, an augmented reality head-mounted display, a laser body motion sensor, an infrared motion sensor, a light camera motion sensor, or an electromagnetic body motion sensor.

4. The computer system of claim 1, wherein the measures of limb acceleration comprise a variance in limb acceleration.

5. The computer system of claim 1, further comprising a task engine, wherein the computer-executable instructions, when executed by the one or more processors, further cause the task engine to initialize a prescribed pattern within the limb movement task to isolate and highlight the movement dynamics predictive of pain.

6. The computer system of claim 1, wherein the computer-executable instructions, when executed, further configure the computer system to receive user input corresponding to an actual, perceived pain.

7. The computer system of claim 1, wherein the computer-executable instructions, when executed, further configure the computer system to perform at least the following:
   re-evaluate results from the limb movement task;
   identify a set of limb movement parameters that comprise a more precise and/or more consistent determinant of different levels and/or amounts of pain than the path smoothness and/or the speed of task performance;
   compare the set of limb movement parameters with a corresponding baseline parameter; and
   update the determined level and/or the amount of pain based on the comparison of the set of limb movement parameters with the corresponding baseline parameter.

8. The computer system of claim 7, wherein the computer-executable instructions, when executed, further configure the computer system to replace the movement dynamics with the set of limb movement parameters, wherein the level and/or the amount of pain is based on a comparison of the set of limb movement parameters with the baseline parameter.

9. The computer system of claim 1, wherein the baseline parameter compared is based on various psycho-social parameters or user-specific bodily state correlated with movement dynamics associated with pain.

10. A method, implemented at a computer system that includes at least one processor, for determining a level and/or an amount of pain in a user based on limb movement dynamics, the method comprising:
monitoring a limb movement task using data received from a limb movement tracking and measuring device;
calculating movement dynamics of limb movement during the limb movement task using the limb movement tracking and measuring device, the movement dynamics comprising:
a path smoothness between distinct points of limb movement related to the limb movement task; and
a speed of task performance, wherein the speed of task performance comprises measures of limb acceleration within the limb movement task or a duration of task performance;
comparing the calculated movement dynamics with a baseline parameter; and
determining a level and/or an amount of pain based on the comparison of the movement dynamics with the baseline parameter.

11. The method of claim 10, wherein the limb movement tracking and measuring device comprises at least one of: a virtual reality head-mounted display, an augmented reality head-mounted display, a laser body motion sensor, an infrared motion sensor, a light camera motion sensor, or an electromagnetic body motion sensor.

12. The method of claim 10, wherein the measures of limb acceleration comprise a variance in limb acceleration.

13. The method of claim 10, further comprising causing a task engine to initialize a prescribed pattern within the limb movement task to isolate and highlight the movement dynamics predictive of pain.

14. The method of claim 10, further comprising receiving user input corresponding to an actual, perceived pain.

15. The method of claim 10, further comprising:
re-evaluating results from the limb movement task;
identifying a set of limb movement parameters that comprise a more precise and/or more consistent determinant of different levels and/or amounts of pain than the path smoothness and/or the speed of task performance;
comparing the set of limb movement parameters with a corresponding baseline parameter; and
updating the determined level and/or the amount of pain based on the comparison of the set of limb movement parameters with the corresponding baseline parameter.

16. The method of claim 15, further comprising replacing the movement dynamics with the set of limb movement parameters, wherein the level and/or the amount of pain is based on a comparison of the set of limb movement parameters with the baseline parameter.

17. The method of claim 10, wherein the baseline parameter compared is based on various psycho-social parameters or user-specific bodily state correlated with movement dynamics associated with pain.

18. A computer program product having stored thereon computer-executable instructions that, when executed by one or more processors of a computer system, cause the computer system to perform at least the following:
monitor a limb movement task using data received from a limb movement tracking and measuring device;
calculate movement dynamics of limb movement during the limb movement task using the limb movement tracking and measuring device, the movement dynamics comprising:
a path smoothness between distinct points of limb movement related to the limb movement task; and
a speed of task performance, wherein the speed of task performance comprises measures of limb acceleration within the limb movement task or a duration of task performance;
compare the calculated movement dynamics with a baseline parameter; and
determine a level and/or an amount of pain based on the comparison of the movement dynamics with the baseline parameter.

19. The computer program product of claim 18, wherein the computer system is integrated into an augmented reality or virtual reality system, and wherein the limb movement tracking and measuring device is a component of the augmented reality or virtual reality system.

20. The computer program product of claim 18, wherein the limb movement tracking and measuring device comprises at least one of: a virtual reality head-mounted display, an augmented reality head-mounted display, a laser body motion sensor, an infrared motion sensor, a light camera motion sensor, or an electromagnetic body motion sensor.

* * * * *